US009327130B2

(12) United States Patent
Marculescu et al.

(10) Patent No.: US 9,327,130 B2
(45) Date of Patent: May 3, 2016

(54) IMPLANTABLE PACEMAKERS CONTROL AND OPTIMIZATION VIA FRACTIONAL CALCULUS APPROACHES

(71) Applicant: CARNEGIE MELLON UNIVERSITY, a Pennsylvania Non-Profit Corporation, Pittsburgh, PA (US)

(72) Inventors: Radu Marculescu, Pittsburgh, PA (US); Paul Bogdan, Los Angeles, CA (US)

(73) Assignee: Carnegie Mellon University, a Pennsylvania Non-Profit Corporation, Pittsburgh, PA (US)

( * ) Notice: Subject to any disclaimer, the term of this patent is extended or adjusted under 35 U.S.C. 154(b) by 187 days.

(21) Appl. No.: 14/252,265

(22) Filed: Apr. 14, 2014

(65) Prior Publication Data

US 2014/0309707 A1    Oct. 16, 2014

Related U.S. Application Data

(60) Provisional application No. 61/853,829, filed on Apr. 12, 2013.

(51) Int. Cl.
*A61N 1/00* (2006.01)
*A61N 1/365* (2006.01)
(Continued)

(52) U.S. Cl.
CPC ........ *A61N 1/36592* (2013.01); *A61B 5/02405* (2013.01); *A61B 5/726* (2013.01); *A61B 5/686* (2013.01); *G06F 19/3437* (2013.01)

(58) Field of Classification Search
CPC .. A61N 1/3627; A61N 1/3684; A61N 1/3682
USPC .......................................................... 607/25
See application file for complete search history.

(56) References Cited

U.S. PATENT DOCUMENTS 6,522,923 B1   2/2003   Turcott
6,567,700 B1   5/2003   Turcott et al.
(Continued)

FOREIGN PATENT DOCUMENTS

EP    0504935 B1   5/1998
EP    2030565 A1   3/2009
(Continued)

OTHER PUBLICATIONS

Bogdan, Paul et al., Implantable Pacemakers Control and Optimization via Fractional Calculus Approaches: A Cyber-Physical Systems Perspective, Proceedings of the 2012 IEEE/ACM Third International Conference on Cyber-Physical Systems, pp. 23-32, IEEE Computer Society, Apr. 17-19, 2012.
(Continued)

*Primary Examiner* — Amanda Patton
*Assistant Examiner* — Philip C Edwards
(74) *Attorney, Agent, or Firm* — David G. Oberdick; Michael G. Monyok

(57) ABSTRACT

Method and system for non-linear modeling of physiological behavior, such as R-R intervals, in implantable devices, such as a rate responsive pacemakers, comprising a comprehensive modeling and optimization methodology based on fractional calculus and constrained finite horizon optimal control theory that allows for allows for fine-grain optimization of pacemaker response to heart rate variations; and the theoretical basis on which a hardware implementation of the fractional optimal controller that can respond to changes in the heart rate dynamics. Present invention describes a fractal approach to pacemaker control based on the constrained finite horizon optimal control problem. This is achieved by modeling the heart rate dynamics via fractional differential equations. Also, by using calculus of variations, the invention describes how the constrained finite horizon optimal control problem can be reduced to solving a linear system of equations. Finally, the invention describes the theoretical basis on which a hardware implementation become possible.

12 Claims, 7 Drawing Sheets

(51) Int. Cl.
*A61B 5/024* (2006.01)
*G06F 19/00* (2011.01)
*A61B 5/00* (2006.01)

(56) References Cited

U.S. PATENT DOCUMENTS

| | | | |
|---|---|---|---|
| 6,993,377 | B2 | 1/2006 | Flick et al. |
| 7,689,283 | B1 | 3/2010 | Schecter |
| 8,280,510 | B2 | 10/2012 | Dyjach et al. |
| 8,321,005 | B2 | 11/2012 | Zhang et al. |

FOREIGN PATENT DOCUMENTS

| | | |
|---|---|---|
| WO | 2008003148 A1 | 1/2008 |
| WO | 2008028004 A2 | 3/2008 |

OTHER PUBLICATIONS

Ghorbani, Mahboobeh et al., A Cyber-Physical System Approach to Artificial Pancreas Design, Proceedings of the Ninth IEEE/ACM/IFIP International Conference on Hardware/Software Codesign and System Synthesis, pp. 1-10, IEEE Press, Sep. 29-Oct. 4, 2013.

IMPLANTABLE PACEMAKERS CONTROL AND OPTIMIZATION VIA FRACTIONAL CALCULUS APPROACHES

CROSS-REFERENCE TO RELATED APPLICATIONS

This application claims priority to U.S. Provisional Application Ser. No. 61/853,829, titled IMPLANTABLE PACEMAKERS CONTROL AND OPTIMIZATION VIA FRACTIONAL CALCULUS APPROACHES, filed Apr. 12, 2013, incorporated by reference herein in its entirety.

STATEMENT REGARDING FEDERALLY-SPONSORED RESEARCH AND DEVELOPMENT

This invention was made with partial government support under grant CCF-0916752 of the National Science Foundation. The government has certain rights in this invention.

FIELD OF THE INVENTION

This invention relates to the field of medical devices, such as cardiac pacemakers, to control physiological behavior. More particularly, the invention relates to using fractional differential equations for modeling heart rate dynamics, and for detection and control of abnormal heart rate patterns.

BACKGROUND OF THE INVENTION

The human heart is a muscle-based organ divided into four chambers: two atria (top chambers holding the blood) and two ventricles (bottom thick-walled chambers meant to help pumping the blood into the circulatory system). When the myocardium and specialized fibers are resting, the heart collects de-oxygenated blood from the body in the right atrium and oxygenated blood from lungs in the left atrium. Then, with each heart beat (which results from a muscle contraction), the blood flows from the right ventricle into the lungs for oxygenation and from the left ventricle into the human body. This entire process of creating a heartbeat is known as the cardiac cycle and is carefully preceded and controlled by a complex electrical mechanism. As shown in FIG. 2, this activity can be recorded on an electrocardiogram as a P-wave (atrial depolarization), as well as QRS complex which corresponds to ventricles depolarization. The cardiac cycle ends with the ventricles repolarization, i.e., a small wave called the T-wave.

Because the R-waves are always the most pronounced ones on an electrocardiogram, the distance between two consecutive R waves (i.e., the R-R interval in FIG. 2) is used by physicians to determine the heart rate activity. Consequently, the study of heart rate variability is extremely important for medical diagnosis. This also motivates our optimal control approach seeking to regulate the magnitude of the R-R intervals and related electro-physiological signals.

Since their invention in 1932, implantable pacemakers have evolved from fixed rate pacemakers (i.e., medical devices delivering an electrical pulse at fixed intervals of time) and demand pacemakers (i.e., medical device triggering an electrical impulse only if a heartbeat is missing), to complex rate responsive pacemakers. The main distinction between the rate responsive pacemakers and their predecessors is that besides the sensory part responsible with sensing the heart beats, they also consist of a control part which is meant to adapt the pacing response as a function of the heart activity. Therefore, designing the control algorithm for heart pacing is a very important and challenging task. For instance, the introduction of extra pacing to an already active heart can be lethal because heart chambers will not have enough time to refill with blood and thus will not provide the necessary amount of oxygenated blood throughout the body. On the other hand, missing heart beats can also lead to critical conditions.

Consequently, based on the characteristics of the proposed control approaches and the state variables which are optimized, the rate responsive pacemakers can be classified as open loop, closed loop, metabolic, and autonomous nervous system (ANS) controllers. For instance, one approach describes a closed loop proportional (P) controller for optimal pacing, which maintains the venous oxygen saturation at a predefined level. Of note, the proposed P-controller relies on a postulated non-linear model that relates the venous oxygen saturation to the heart rate. Along the same lines, another approach discusses a closed loop pacing approach based on regulating the atrial-ventricular conduction time (AVCT). At the heart of its approach lies the assumption that the dynamics of AVCT can be modeled as a linear time invariant system. Employing a similar closed-loop process control, yet another approach proposes a classical proportional-integral derivative (PID) controller for ensuring that the entire system consisting of the heart rate activity and pacing pulse achieves a targeted R-R interval. More precisely, its PID controller uses the error difference between the monitored and the predefined target R-R interval to compute the necessary amplitude of the atrio-ventricular node vagal stimulation. Using the same error difference between the observed and targeted R-R interval, another approach proposes a proportional integral (PI) closed loop controller to determine the frequency of stimulation. Open loop pacing rate is determined only by the current state of heart rate by using a predefined model with no feedback from changes in the system and no observation of the output. Closed loop pacing rate is determined by using feedback information from the output of the systems (in particular, the heart rate activity). Metabolic pacing depends on metabolism and/or respiratory system. Autonomous nervous system pacing is influenced by the autonomous nervous system activity.

More recently, another approach assumes that the heart rate activity can be modeled by a second order transfer function and present a proportional plus derivative controller for regulating the heart rate.

A further approach proposes a nonlinear heart beat control algorithm that uses concepts of proportional gain and norm. Alternatively, one variant uses the fuzzy control theory to regulate pacing while patient respiratory rate and temperature are used as state variables. In contrast to these approaches, still another approach uses an optimal control approach to regulate the heart rate and the sympathetic activity while assuming that the blood pressure is the state variable.

Despite this significant body of work, current state-of-the-art pacing algorithms assume that the heart rate (and other relevant physiological processes) can be modeled via linear state equations. However, by relying on de-trended fluctuation analysis, one can observe that the R-R intervals exhibit a fractal behavior and thus cannot be well approximated by such linear models. To overcome this limitation, the present invention describes control algorithms of rate responsive pacemakers that rely on fractal dynamical equations using concepts from fractional calculus.

SUMMARY OF THE INVENTION

This present invention describes a fractal approach to pacemaker control based on the constrained finite horizon optimal control theory. This is first achieved by modeling the heart rate dynamics via fractional differential equations. Then, by using calculus of variations, the invention describes how the constrained finite horizon optimal control problem can be reduced to solving a linear program. This allows for a unique type of fine-grain optimization of pacemaker response to heart rate variations. Finally, the invention describes the theoretical basis on which a hardware implementation becomes possible.

DETAILED DESCRIPTION OF THE INVENTION

The present invention describes a method for determining and controlling physiological behavior, such as heart rate abnormalities, by using a fractal optimal control approach. The example described herein is for a pacemaker application to control heart rate abnormalities. However, the invention is not to be limited to a pacemaker application.

Basics of Fractional Calculus

The origins of fractional calculus date back to the correspondence between L'Hopital and Leibniz in which they debated the meaning of a 0.5 order differentiation. Over the years, fractional calculus has found applications in physics (e.g., viscoelasticity, dielectric polarization, heat transfer phenomena) and engineering (e.g., control bioengineering, traffic modeling, game theory).

Broadly speaking, fractional (or fractal) calculus deals with functional differentiation and integration of arbitrary orders. Unlike classical (i.e., integer order) calculus, fractional derivatives directly incorporate the dynamical characteristics (i.e., fractal behavior) of any target process x(t) (e.g., R-R intervals, flow of oxygenated blood) through a weighted sum denoting the contribution of the previous events $x(\tau)$, for any $\tau \in [0, t]$:

$$\frac{d^\alpha x(t)}{dt^\alpha} = \frac{1}{\Gamma(n-\alpha)} \frac{d^n}{dt^n} \int_0^t \frac{x(\tau)}{(t-\tau)^{\alpha-n+1}} d\tau, \quad (1)$$

where $\alpha$ is the fractional order of the derivative and $\Gamma(n-\alpha)$ is the Gamma function. This continuous time definition of fractional derivative can also be written in discretized form via the Grunwald-Letnikov formula:

$$\frac{d^\alpha x(t)}{dt^\alpha} = \lim_{\Delta t \to 0} \frac{1}{\Delta t^\alpha} \sum_{j=0}^{[t/\Delta t]} (-1)^j \binom{\alpha}{j} x(t - j\Delta t) \quad (2a)$$

where $\Delta t$ is the time increment, $[t/\Delta t]$ represents the integer part of the ratio between the t and $\Delta t$. Equations (1) (continuous) and (2a) (discrete) capture directly the role of the power law observed in the time differences (i.e., $(t-\tau)^{n-\alpha-1}$) and allows not only for a more accurate description of the time dynamics of various physiological processes x(t), but also for a better optimization; this issue is discussed in the next section.

Basics of R-R Interval Measuring and of the Identification of Fractional Model Parameters In order to measure the R-R interval, the pacemaker senses the voltage produced by the heart when it contracts. This voltage is usually small in the range of a millivolts. The pacemaker uses a sensitivity level (sometimes referred as threshold voltage) to detect R-waves. In other words if the sensed ECG voltage exceeds this threshold, then an R-wave is detected and the clock starts counting until the next R-wave is encountered (e.g., the R-R interval). This threshold corresponds to the minimum current to pace the ventricle. See Block 30 of FIG. 1.

Figure 1:
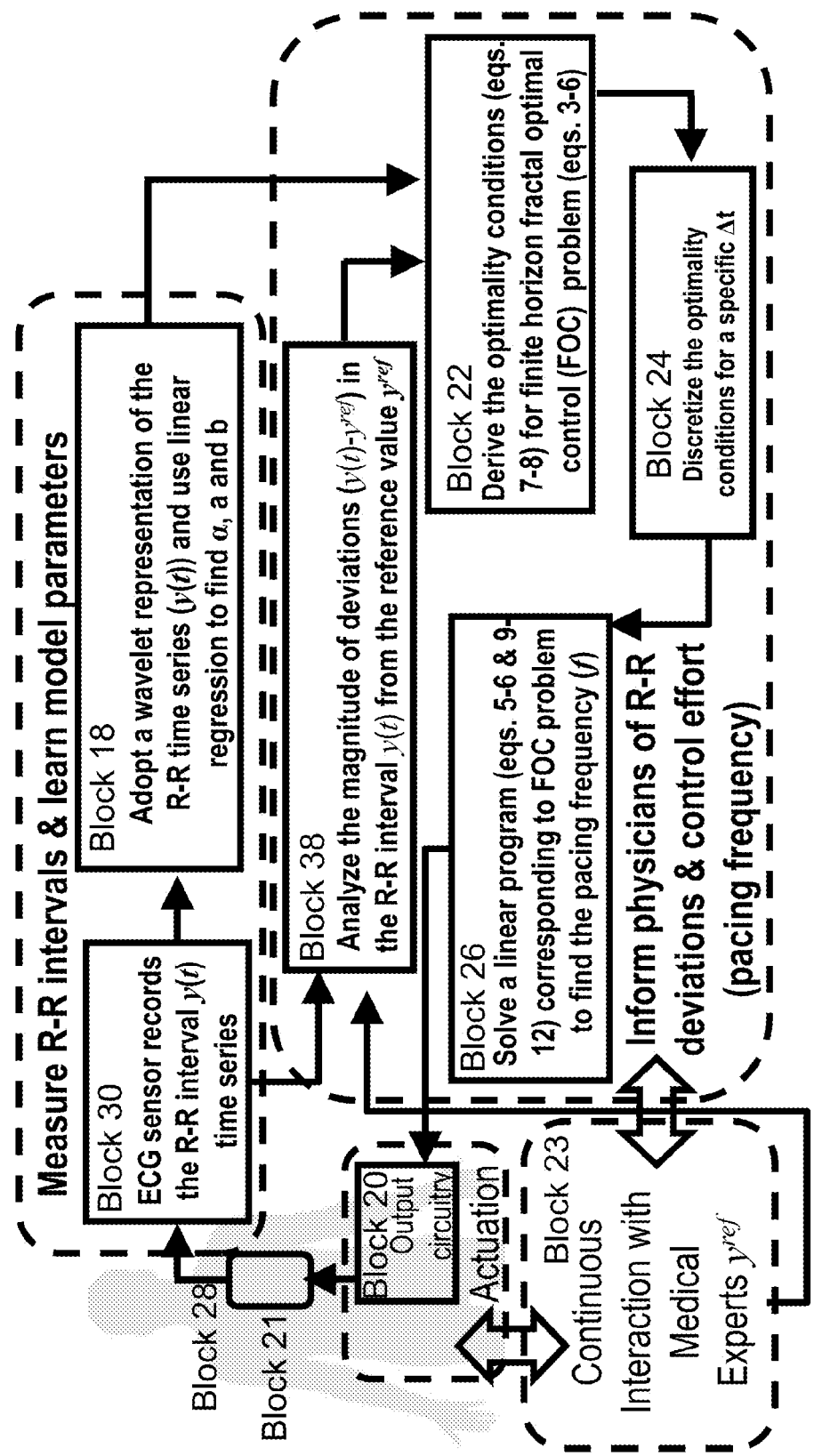
FIG. 1 is a schematic of one embodiment of the present invention illustrating a Cyber-physical system approach to pacemaker design: Accurate monitoring and continuous interaction with medical experts/devices (Block 46) allows for better modeling (Blocks 18 and 38) and control (Blocks 22, 24, and 26) approaches of rate adaptive pacemakers.
Figure 2:
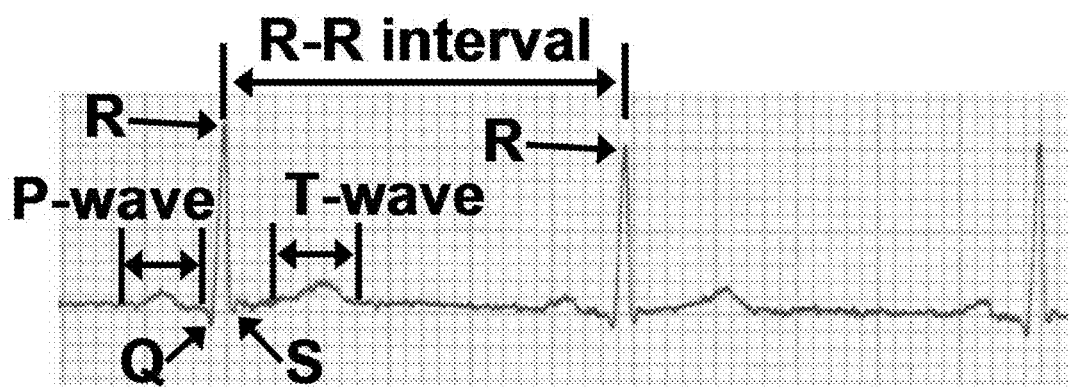
FIG. 2 illustrates a short electrocardiogram showing the heart activity of three beats and the P-wave (atrial depolarization), QRS complex (ventricles depolarization) and T wave (ventricles repolarization). The R-R interval is the time interval between two consecutive heart beats represented in the electrocardiogram by two consecutive R-waves. The variability observed in the R-R intervals is essential for medical diagnosis.

Now turning to Block 18 of FIG. 1, upon using the Grunwald-Letnikov formula, the continuous time fractional differential equation (4) is used to model the dynamics of the R-R intervals can be expressed as follows:

$$\frac{1}{\Delta t^\alpha} \sum_{j=0}^{[t/\Delta t]} (-1)^j \binom{\alpha}{j} x(t - j\Delta t) = ax(t) + bu(t) \quad (2b)$$

In order to estimate the model parameters, $T=2^J$ observations (measured R-R intervals) are used. Using the Daubechies discrete wavelet transform of order four, the wavelet coefficients $d_{j,k}$ from the T measured R-R intervals are calculated. The wavelet coefficients $d_{j,k}$ are computed via the following formula:

$$d_{j,k} = 2^{j/2} \sum_{i=0}^{T} y(t) \varphi(2^j t - k),$$

where $\varphi$ is the Daubechies wavelet. (Mark J. Jensen, An alternative maximum likelihood estimator of long-memory processes using compactly supported wavelets, Journal of Economic Dynamics & Control, 24 (2000) 361}387; Y. K. Tse, V. V. Anh, Q. Tieng, Maximum likelihood estimation of the fractional differencing parameter in an ARFIMA model using wavelets, Mathematics and Computers in Simulation 59 (2002) 153-161.) In addition, the wavelet coefficients are Gaussian distributed with $N(0, \sigma^2 2^{-2j\alpha})$ are assumed, where the $\sigma^2 2^{-2j\alpha}$ term gives the autocovariance RU) at scale j. Alternatively, the autocovariance can be written as $\ln(R(j))=2 \ln(\sigma) - 2j\alpha \ln(2)$. In terms of the wavelet coefficients, the autocovariance R(j) can be written as follows:

$$R(j) = \frac{1}{2^j} \sum_{k=0}^{2^j - 1} d_{j,k}^2.$$

Consequently, in order to find parameter a, a linear regression is solved to find the slope of how the logarithm of the empirically estimated autocovariance changes as a function of the logarithm of the scale which is provided by the next relation: $\ln(R(j))=2 \ln(o) - 2j\alpha \ln(2)$. Knowing $\alpha$, the coefficients under the summation term in the left hand side of equation (3) can be computed. Relying on a linear regression over the same T observations, we can compute the parameters a and b in equation (3).

Block 38 analyzes if deviations from a reference value provided by medical expert in Block 23 are detected. If there are no deviations, then the system waits for the next R-R interval measurement and processing terminates on the current R-R interval. Block 18 uses wavelets and linear regression (solving a linear program) to identify the parameters of the mathematical model. Of note, depending on the dynamics of the heart rate variability which is encompassed in the parameter a, the model can consist of a fractional differential equation or an integer order differential equation. Based on the magnitude of deviations detected in Block 38 and the recommendation of the physician (Block 23), the pacemaker can solve in the second part either an ISE-based constrained fractal optimal controller (less aggressive control) or an ITSE-based constrained fractal optimal controller (more aggressive). If an ISE-based fractal controller is chosen, then the control approach of the pacemaker relies on deriving the optimality conditions (Block 22*a*), discretizing the optimality conditions (Block 24*a*) and solving a linear program corresponding to the ISE-based constrained fractal optimal controller (Block 26*a*). If an ITSE-based fractal controller is chosen, then the control approach of the pacemaker relies on deriving the optimality conditions (Block 22*b*), discretizing the optimality conditions (Block 24*b*) and solving a linear program corresponding to the ITSE-based constrained fractal optimal controller (Block 26*b*). In the third part, the solution of either the ISE-based constrained fractal optimal controller or the ITSE-based constrained fractal optimal controller is applied by the actuator (Block 20) to the heart. On the same time, this pacing frequency is communicated via wireless and internet to the physician (Block 23) for further analysis and medical evaluation.

Fractional Calculus Based Modeling and Optimal Control of Heart Rate Activity

The present invention takes into account that the heart rate processes display a fractal behavior and can be modeled via fractional differential equation. This approach represents a major departure from the traditional modeling approaches used in control (dynamic) optimization field. The present invention brings the magnitude of R-R intervals to a given reference value provided by a medical expert (Block 46 in FIG. 1) from either very large or very small values which are signs of heart disease (i.e., bradycardia or tachycardia). Of note, although the present invention describes the optimal control problem only for two different cost functions, those skilled in the art will recognize that the invention can be extended to other cost functions and control signals (e.g., magnitude of the pacing voltage applied to either atria or ventricles).

A. Finite Time Fractal Optimal Control with Integral of Squared Tracking Error (ISE) Criterion The present invention describes an ISE-based constrained finite horizon fractal optimal control approach (see Blocks 22*a*, 24*a* and 26*a* in FIG. 7) to heart rate regulation problem. More precisely, given an initial time $t_i$ and a final time $t_f$, the goal of the controller is to find the optimal control signal, i.e., the frequency of the pacing events, which minimizes the quadratic cost of observing deviations in either the magnitude of R-R intervals or heart rate activity from a predefined reference value, as well as the magnitude of pacing frequency, as shown below:

$$\min_{f(t)} \int_{t_i}^{t_f} \left\{ \frac{w}{2}[y(t) - y^{ref}(t)]^2 + \frac{z}{2} f^2(t) \right\} dt \quad (3)$$

$$\frac{d^\alpha y(t)}{dt^\alpha} = a(t)y(t) + b(t)f(t), \quad (4)$$

subject to the following constraints:

$$y(t_i) = y_0, \ y(t_f) = y_0, \ 0 \le y^{min} \le y(t) \le y^{max} \le 1 \quad (5)$$

$$f^{min} \le f(t) \le f^{max}$$

where y(t) represents the heart rate activity seen as a state variable and measured in Block 30, $y^{ref}(t)$ denotes the reference values that need to be achieved in terms of heart rate activity and is provided by medical expert Block 46, f(t) is the pacing frequency, w and z are the weighting coefficients for the quadratic error and magnitude of the control signal, respectively, in the cost function, α is the exponent of the fractional order derivative characterizing the dynamics of the heart rate activity y(t) being estimated by Block 18, a(t) and b(t) are weighting coefficients for the heart activity and pacing frequency being estimated by Block 18, $y^{min}$ and $y^{max}$ are the minimum and maximum bounds on heart rate activity y(t) being provided by physician Block 46, $y(t_i)$ is the initial condition, $y(t_f)$ is the final condition, $f^{min}$ and $f^{max}$ are the minimum and maximum allowed bounds on pacing frequency f(t). Physician (Block 46) provided parameters including $y^{ref}$, w, z $y^{min}$, $y^{max}$, $f^{min}$, and $f^{max}$ (see FIG. 8).

By focusing on the squared difference between the actual and the reference value in Eq. (3), the optimal controller minimizes the chances of getting either positive or negative deviations from a predefined reference. In other words, the cost functional in Eq. (3) penalizes any deviations from the reference value and large magnitudes in the control signal. The use of the integral of squared difference between the actual and the reference heart rate is also attractive because of two reasons: first, it simplifies to linear equations when evaluating the optimality conditions. Second, the integral of squared error is in general robust to parameter variations. Note that unlike other general formulations of optimal control, in this setup there are very specific initial and final values summarized in Eq. (5). Consequently, the role of the controller is to determine the right pacing frequency which drives the system from one initial state (labeled as life-threatening) to a final state (labeled as safe).

Note also that in both equations (4) and (6), minimum and maximum bounds are imposed on the expected R-R intervals and the delivered pacing frequencies. These bounds are necessary because they prevent the optimal control algorithm from driving the heart muscle system at excessive pacing rates.

To solve the above optimal control problem, the present invention utilizes concepts from the optimization theory and constructs first the Lagrangian functional, L(y, f, λ, $\beta_1$, $\xi_1$, $\beta_2$, $\xi_2$) (consisting of the initial cost function in Eq. (3), the fractal dynamical equation (4) and the constraints in Eqs. (5) and (6) multiplied by Lagrange multipliers), as follows:

$$L = \int_{t_i}^{t_f} \left\{ \frac{w[y(t) - y^{ref}(t)]^2}{2} + \frac{zf^2(t)}{2} + \beta_1(f - f^{min} - \xi_1) - - \right.$$

$$\left. \lambda \left[ \frac{d^\alpha y(t)}{dt^\alpha} - a(t)y(t) - b(t)f(t) \right] + \beta_2(f^{max} - f - \xi_2) \right\} dt \quad (7)$$

where λ, $\beta_1$, and $\beta_2$ are the Lagrange multipliers associated with the dynamical state equation for y(t) and the constraints imposed on the control variable f, $\xi_1$ and $\xi_2$ are the slack variables needed to transform the inequality bounds into equality constraints on the control variable f. The reason for introducing the Lagrange multipliers λ, $\beta_1$, and $\beta_2$ and encapsulating the fractal dynamical equation (4) and the constraints in Eqs. (5), and (6) into a single optimization function is to transform the constrained problem into an unconstrained minimization.

By expanding the Lagrange function in Eq. (7) via the Taylor formula and considering that it attains its minimum in the vicinity of τ=0, i.e., ∂L/∂τ=0, the following relations are obtained:

$$\frac{\partial L}{\partial y} +_t D^\alpha_{t_f} \frac{\partial L}{\partial_{t_i} D^\alpha_t y} = 0, \frac{\partial L}{\partial f} = 0, \frac{\partial L}{\partial \lambda} = 0, \frac{\partial L}{\partial \beta_1} = 0, \frac{\partial L}{\partial \beta_2} = 0 \quad (8)$$

where $_{t_i}D^\alpha_t$ and $_t D^\alpha_{t_f}$ are the fractional derivatives operating backward and forward in time, respectively. This is represented by Block 22 in FIG. 1.

In order to solve the relations in Eq. (8) (see the Block 24 in FIG. 1), this invention discretizes the interval $[t_i, t_f]$ into N intervals of size $\Delta t=(t_f-t_i)/N$ and use the formula in Eq. (2a) to construct a linear system as follows:

$$\sum_{i=0}^{k} \frac{(-1)^i}{\Delta t^\alpha} \binom{\alpha}{i} y((k-i)\Delta t) - a(k\Delta t)y(k\Delta t) + \frac{b(k\Delta t)}{z(k\Delta t)}\lambda(k\Delta t) + \quad (9)$$

$$\frac{b(k\Delta t)}{z(k\Delta t)}\beta_1(k\Delta t) - \frac{b(k\Delta t)}{z(k\Delta t)}\beta_2(k\Delta t) = 0, k = 1, \ldots, N$$

$$\frac{\beta_2(k\Delta t) - \beta_1(k\Delta t) - b(k\Delta t)\lambda(k\Delta t)}{z(k\Delta t)} - \xi_1(k\Delta t) = f^{min}, k = 1, \ldots, N \quad (10)$$

$$\frac{\beta_2(k\Delta t) - \beta_1(k\Delta t) - b(k\Delta t)\lambda(k\Delta t)}{z(k\Delta t)} + +\xi_2(k\Delta t) = f^{max}, k = 1, \ldots, N \quad (11)$$

$$\sum_{i=0}^{N-k} \binom{\alpha}{i}\frac{(-1)^i \lambda((k+i)\Delta t)}{\Delta t^\alpha} - w(k\Delta t)[y(k\Delta t) - y^{ref}(k\Delta t)] - \quad (12)$$

$$a(k\Delta t)\lambda(k\Delta t) + \frac{\lambda(\Delta t N)(t_f - t_i - k\Delta t)^{-\alpha}}{\Gamma(1-\alpha)} = 0, k = N-1, \ldots, 0$$

Figure 7:
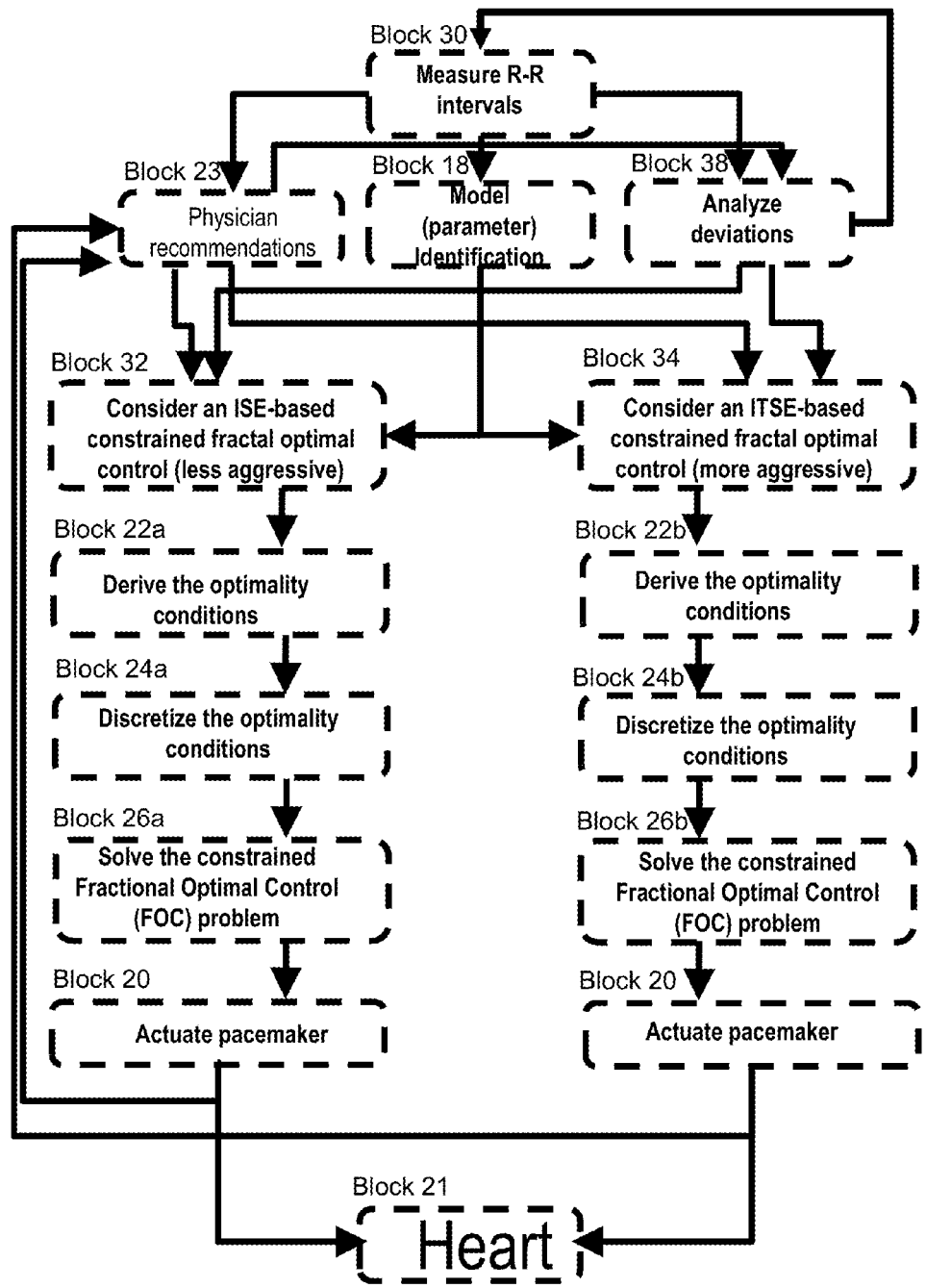
FIG. 7 is a logic flow diagram of one embodiment of the present invention and consists of four main parts; In the first part, the heart signals (Block 28 in FIG. 1) are sensed and R-R intervals are measured (Block 30). Concomitantly, the current measured R-R interval is send to two blocks: Firstly, Block 38 analyzes if deviations from a reference value provided by medical expert in Block 23 are detected. Secondly, Block 18 uses wavelets and linear regression (solving a linear program) to identify the parameters of the mathematical model. Of note, depending on the dynamics of the heart rate variability which is encompassed in the parameter a, the model can consist of a fractional differential equation or an integer order differential equation. Based on the magnitude of deviations detected in Block 38 and the recommendation of the physician (Block 23), the pacemaker can solve in the second part either an ISE-based constrained fractal optimal controller (less aggressive control) or an ITSE-based constrained fractal optimal controller (more aggressive). If an ISE-based fractal controller is chosen, then the control approach of the pacemaker relies on deriving the optimality conditions (Block 22a), discretizing the optimality conditions (Block 24a) and solving a linear program corresponding to the ISE-based constrained fractal optimal controller (Block 26a). If an ITSE-based fractal controller is chosen, then the control approach of the pacemaker relies on deriving the optimality conditions (Block 22b), discretizing the optimality conditions (Block 24b) and solving a linear program corresponding to the ITSE-based constrained fractal optimal controller (Block 26b). In the third part, the solution of either the ISE-based constrained fractal optimal controller or the ITSE-based constrained fractal optimal controller is applied by the actuator (Block 20) to the heart. On the same time, this pacing frequency is communicated via wireless and internet to the physician (Block 23) for further analysis and medical evaluation.

Now turning to FIG. 7 illustrating a logic flow diagram of one embodiment of the present invention and consists of four main parts; In the first part, the heart signals (Block 28 in FIG. 1) are sensed and R-R intervals are measured (Block 30). Concomitantly, the current measured R-R interval is send to two blocks: Firstly, Block 38 analyzes if deviations from a reference value provided by medical expert in Block 23 are detected. Secondly, Block 18 uses wavelets and linear regression (solving a linear program) to identify the parameters of the mathematical model. Of note, depending on the dynamics of the heart rate variability which is encompassed in the parameter a, the model can consist of a fractional differential equation or an integer order differential equation. Based on the magnitude of deviations detected in Block 38 and the recommendation of the physician (Block 23), the pacemaker can solve in the second part either an ISE-based constrained fractal optimal controller (less aggressive control) or an ITSE-based constrained fractal optimal controller (more aggressive). If an ISE-based fractal controller is chosen, then the control approach of the pacemaker relies on deriving the optimality conditions (Block 22*a*), discretizing the optimality conditions (Block 24*a*) and solving a linear program corresponding to the ISE-based constrained fractal optimal controller (Block 26*a*). If an ITSE-based fractal controller is chosen, then the control approach of the pacemaker relies on deriving the optimality conditions (Block 22*b*), discretizing the optimality conditions (Block 24*b*) and solving a linear program corresponding to the ITSE-based constrained fractal optimal controller (Block 26*b*). In the third part, the solution of either the ISE-based constrained fractal optimal controller or the ITSE-based constrained fractal optimal controller is applied by the actuator (Block 20) to the heart. On the same time, this pacing frequency is communicated via wireless and internet to the physician (Block 23) for further analysis and medical evaluation. Note: If there are no deviations analyzed in Block 38, then the system waits for the next R-R interval measurement and processing terminates on the current R-R interval.

Figure 8:
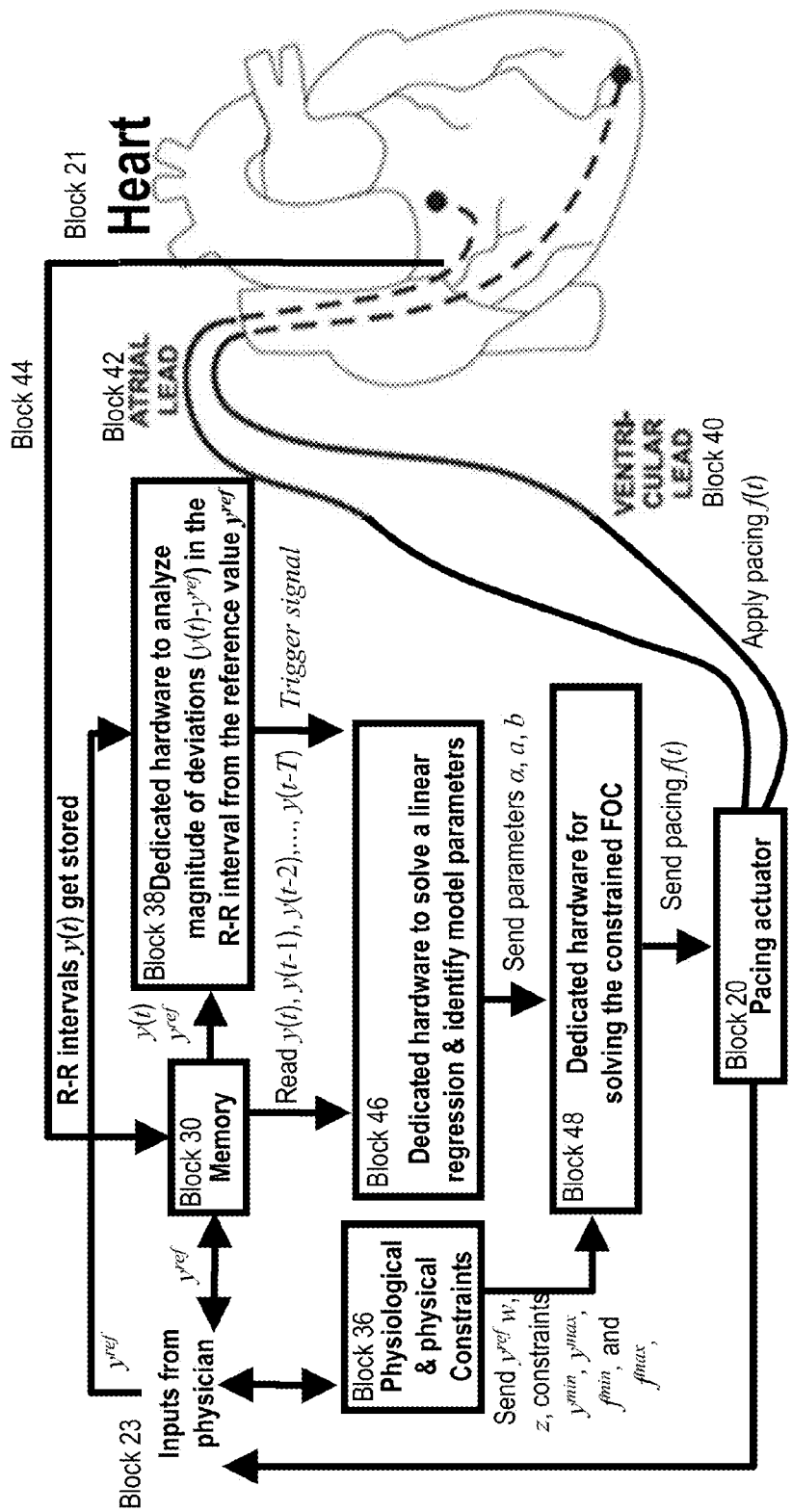
FIG. 8 is a block Diagram of the Hardware Architecture showing a control signal—pacing frequency—necessary to be followed by the optimal controller module (described by equations (13) through Eq. (16)) of the pacemaker in order to increase the R-R intervals and reduce the heart rate from approximately 100 to 75 beats per minute. Generally speaking, the measured R-R intervals from Blocks 44 and 30 get transmitted to the physician (Block 23), dedicated hardware for analyzing the magnitude of the deviations ($y(t)-y^{ref}$) (Block 38) and the dedicated hardware for identifying the model parameters (Block 46). The dedicated hardware for analyzing the magnitude of the $y(t)-y^{ref}$ deviations consists of an arithmetic logic unit performing a subtraction operation. As explained in this patent application, the dedicated hardware for identifying the parameters of the model consists of wavelets filters and a linear program solver to find a, a and b. If Block 38 detects any deviations, then a trigger is signaled the parameters of the model in Block 46 are identified and the next step is to find the optimal pacing frequency via the dedicated hardware that solves the constrained fractal optimal controller in Block 48, else the system waits for the next R-R interval if Block 38 does not detect any deviations. When solving the constrained fractal optimal controller, Block 48 receives reference value and parameter constraints from the physician in Block 23. The solution of the constrained fractal optimal controller in Block 48 is then applied by the actuator in Block 20 to the heart (Block 21) via atrial (Block 42) and ventricular (Block 40) leads. Of note, although in this hardware description diagram we assumed that the fractal optimal controller is completely implemented via an application (dedicated) specific integrated circuit, similar results can be obtained if the controller is implemented in software and ported to an embedded processor. The rationale for choosing this hardware implementation approach is two-fold: First, it offers a more compact and more power-efficient implementation solution of the memory and logic of the pacemaker controller. Secondly, we aimed at testing the feasibility of implementing our proposed constrained fractal optimal controller.

Now turning to FIG. 8 illustrating a block Diagram of the Hardware Architecture showing a control signal—pacing frequency—necessary to be followed by the optimal controller module (described by equations (13) through Eq. (16)) of the pacemaker in order to increase the R-R intervals and reduce the heart rate from approximately 100 to 75 beats per minute. Generally speaking, the measured R-R intervals from Blocks 44 and 30 get transmitted to the physician (Block 23), dedicated hardware for analyzing the magnitude of the deviations ($y(t)-y^{ref}$) (Block 38) and the dedicated hardware for identifying the model parameters (Block 46). The dedicated hardware for analyzing the magnitude of the $y(t)-y^{ref}$ deviations consists of an arithmetic logic unit performing a subtraction operation. As explained in this patent application, the dedicated hardware for identifying the parameters of the model consists of wavelets filters and a linear program solver to find a, a and b. If Block 38 detects any deviations then a trigger is signaled the parameters of the model in Block 46 are identified and the next step is to find the optimal pacing frequency via the dedicated hardware that solves the constrained fractal optimal controller in Block 48, else the system waits for the next R-R interval if Block 38 does not detect any deviations. When solving the constrained fractal optimal controller, Block 48 receives reference value and parameter constraints from the physician in Block 23. The solution of the constrained fractal optimal controller in Block 48 is then applied by the actuator in Block 20 to the heart (Block 21) via atrial (Block 42) and ventricular (Block 40) leads. Of note, although in this hardware description diagram we assumed that the fractal optimal controller is completely implemented via an application (dedicated) specific integrated circuit, similar results can be obtained if the controller is implemented in software and ported to an embedded processor. The rationale for choosing this hardware implementation approach is two-fold: First, it offers a more compact and more power-efficient implementation solution of the memory and logic of the pacemaker controller. Secondly, we aimed at testing the feasibility of implementing our proposed constrained fractal optimal controller. The dedicated hardware can include a processor (not shown) in any commercially available form, such as, but not limited to, an embedded processor, micro-processor, a programmable logic controller, or electrically circuitry capable of performing calculations.

In summary, the constrained finite horizon fractal optimal control defined in Eqs. (3) through (6) can be reduced to solving a linear programming problem (given by Eqs. (9), (10), (11), and (12)) (see Block 26 in FIG. 1) and so it does not add a significant complexity compared to classical linear system theory approaches. The solution (output) of the linear program in Block 26 from FIG. 1 is applied by the actuator (Block 20 in FIG. 1) to the heart 21 in FIG. 8. In addition, this constrained finite horizon fractal optimal control can address some of the American Heart Association desideratum for optimal control algorithms that find the right pacing frequency, output voltage, pulse width, or atrio-ventricular delays that can improve the patient quality-of-life and battery longevity. To sustain a continuous quality-of-life aware pacing, the pacemaker reports via wireless/WIFI connectivity and internet connection the observed deviations, the measured R-R intervals and the computed pacing frequencies to the medical experts 23 in FIG. 1.

B. Finite Time Fractal Optimal Control with Integral of Squared Time Multiplied by Squared Tracking Error (ITSE) Criterion Despite its analytical tractability, the finite time optimal control problem with integral of the squared difference between the actual and reference value of the process has the drawback that in some cases it can present large overshoots and oscillations. In addition, besides the magnitude of the error existing between the actual and the reference values, also the time at which this error occurs is of significant importance. As an alternative to the integral of the difference between the actual and the reference values, an optimization criterion involving the integral of the squared time multiplied by the squared tracking error (ITSE) is considered. This approach is meant to penalize any overshoot or oscillation that might appear in the cost function close to the final time $t_f$. Consequently, the augmented finite horizon fractal optimal control problem seeks to minimize the following cost function:

$$\min_{f(t)} \int_{t_i}^{t_f} \left\{ \frac{w}{2}[t(y(t) - y^{ref}(t))]^2 + \frac{z}{2}f^2(t) \right\} dt \quad (13)$$

subject to the following dynamical equation:

$$\frac{d^\alpha y(t)}{dt^\alpha} = a(t)y(t) + b(t)f(t), \quad (14)$$

and to the following constraints:

$$y(t_i)=y_0,\ y(t_f)=y_0,\ 0 \leq y^{min} \leq y(t) \leq y^{max} \leq 1 \quad (15)$$

$$f^{min} \leq f(t) \leq f^{max} \quad (16)$$

where y(t) represents the heart rate activity seen as a state variable, $y^{ref}(t)$ denotes the reference values that need to be achieved in terms of heart rate activity, f(t) is the pacing frequency, w and z are the weighting coefficients for the quadratic error and magnitude of the control signal, respectively, in the cost function, α is the exponent of the fractional order derivative characterizing the dynamics of the heart rate activity y(t), a(t) and b(t) are weighting coefficients for the heart activity and pacing frequency, $y^{min}$ and $y^{max}$ are the minimum and maximum bounds on heart rate activity y(t), y($t_i$) is the initial condition, y($t_f$) is the final condition, $f^{min}$ and $f^{max}$ are the minimum and maximum allowed bounds on pacing frequency f(t). Physician provided parameters include $y^{ref}$, w, z $y^{min}$, $y^{max}$, $y^{min}$, and $f^{max}$.

Employing concepts from the theory of constrained optimization and calculus of variations and discretizing the optimality conditions (i.e., differential equations), the following system of equations are obtained:

$$\sum_{i=0}^{k} \frac{(-1)^i}{\Delta t^\alpha} \binom{\alpha}{i} y((k-i)\Delta t) - a(k\Delta t)y(k\Delta t) + \frac{b(k\Delta t)^2}{z(k\Delta t)}\lambda(k\Delta t) + \quad (17)$$

$$\frac{b(k\Delta t)\beta_1(k\Delta t)}{z(k\Delta t)} - \frac{b(k\Delta t)\beta_2(k\Delta t)}{z(k\Delta t)} = 0,\ k=1,\ldots,N$$

$$\sum_{i=0}^{N-k} \binom{\alpha}{i} \frac{(-1)^i \lambda((k+i)\Delta t)}{\Delta t^\alpha} - \quad (18)$$

$$w(k\Delta t)(k\Delta t)^2[y(k\Delta t) - y^{ref}(k\Delta t)] - -a(k\Delta t)\lambda(k\Delta t) +$$

$$\frac{\lambda(\Delta tN)(t_f - t_i - k\Delta t)^{-\alpha}}{\Gamma(1-\alpha)} = 0,\ k=N-1,\ldots,0$$

$$\frac{\beta_2(k\Delta t) - \beta_1(k\Delta t) - b(k\Delta t)\lambda(k\Delta t)}{z(k\Delta t)} - \xi_1(k\Delta t) = f^{min},\ k=1,\ldots,N \quad (19)$$

$$\frac{\beta_2(k\Delta t) - \beta_1(k\Delta t) - b(k\Delta t)\lambda(k\Delta t)}{z(k\Delta t)} + \xi_2(k\Delta t) = f^{max},\ k=1,\ldots,N \quad (20)$$

As one can observe from equations (17), (18), (19), and (20), the optimal control problem reduces to solving a linear program which computes the y and λ values for a predefined set of discretization steps. Of note, the size of the linear program depends on the number of discretization steps.

Eqs. (13)-(20) are interchangeable with Eqs. (3), (4), (5), (6), (9), (10), (11), and (12), respectively with respects to Blocks 22, 24, and 26 of FIG. 1. Eqs (7) and (8) are used in calculations for Finite Time Fractal Optimal Control with Integral of Squared Tracking Error Criterion and Finite Time Fractal Optimal Control with Integral of Squared Time Multiplied by Squared Tracking Error Criterion.

Experimental Results

An important requirement of optimal control approaches is to rely on accurate models of the dynamical system or state variables of interest to the designer. Consequently, in our evaluation of the inventive method, we first estimated the parameters corresponding to a non-fractal and a fractal model and analyzed the goodness-of-fit of each approach. More precisely, we performed a hypothesis testing by investigating whether or not the observed data can be modeled via a specific model. In this context, the goodness-of-fit measures (via the P-value) the discrepancy between the real measurements and the model predictions. Next, we provided a complete numerical analysis of the proposed fractal optimal control problems. The P-value is a goodness-of-fit metric. A small P-value (below the significance value) allows us to reject the null hypothesis (the data follows a certain distribution or can be modeled via an ARMA type with specific parameters).

| Heart Rate Time Series ID | Classical (Non-Fractal) Model | | | | Fractal Model | | | | |
|---|---|---|---|---|---|---|---|---|---|
| | Parameters of the model | | Goodness-of-fit | | Parameters of the model | | | Goodness-of-fit | |
| | a | b | P-value | Test statistic | α | a | b | P-value | Test statistic |
| 1 | 0.9665 | 0.0267 | 0 | 61.127 | 0.6226 | 0.1613 | −0.1284 | 1 | 0.2754 |
| 2 | 0.979 | 0.0193 | 0 | 30.031 | 0.7762 | 0.0355 | −0.0326 | 1 | 0.2564 |
| 3 | 0.9513 | 0.0403 | 0 | 120.880 | 0.707 | 0.1255 | −0.1038 | 0.51 | 0.3182 |
| 4 | 0.9525 | 0.0409 | 0 | 73.945 | 0.7258 | 0.1105 | −0.0951 | 1 | 0.2544 |
| 5 | 0.9663 | 0.0286 | 0 | 88.339 | 0.699 | 0.0643 | −0.0546 | 1 | 0.2714 |

A. Parameter Identification of Fractional Calculus Models

TABLE I (below) is a comparison between a non-fractal model (1-step arma) and a fractal model (see equation (4)) in terms of the estimated parameters and the goodness-of-fit obtained for five time series of heart rate activity. The R-R interval time series are obtained for healthy individuals. Except the time series with id 3, all other heart rate activity series can be modeled through a fractional order differential equation of the type presented in equation (4). This is justified by the estimated P-values and test statistics.

To make the discussion of our evaluative approach more concrete, we considered two types of models: First, we modeled the heart rate through a first order differential equation, estimate the corresponding parameters (i.e., a and b), and computed the goodness-of-fit between the actual measurements and the obtained model. Second, we assumed that over a finite time interval the heart rate can be modeled through a fractional order differential equation similar to the one presented in equation (4), estimated the parameters a, a, and b and report its goodness-of-fit.

Table 1 summarizes the estimated parameters and the goodness-of-fit results for both non-fractal and fractal models used to model the heart rate dynamics of healthy individuals. To discriminate in terms of accuracy between the two models, we use the goodness-of-fit at 0.05 statistical significance level. This implies that we perform a null hypothesis testing against each model and if the P-value computed for the considered model is below 0.05 level, then with 95% confidence we reject the model as a good fit for the data. Note that this statistical approach proves to be a more robust way of validating models than relying on mean square method. By comparing the P-values in the fourth and ninth columns, we can draw the following conclusions:

The modeling approach of heat rate processes via a fractional differential equation (as shown in equation (4)) cannot be rejected. The model is superior to the one based on first order derivative for all five heart rate times both in terms of P-values and test statistics. The modeling of heart rate dynamics via a first order derivative type of model is strongly rejected by the observed null P-values and high test statistic results. For completeness, in Table 2, we investigate the goodness-of-fit between a non-fractal model (i.e., first order differential equation) and a fractal one (based on fractional derivative as shown in equation (4)) for an individual suffering from atrial fibrillation. As one can notice, although the magnitude of the P-values increases compared to the healthy individuals, their values are smaller than the 0.05 significance level allowing us to reject the hypothesis that we can model such heart activity time series via a non-fractal equation. In contrast, the P-values for the fractional order derivative based model are significantly higher allowing the possibility of being a good fitting model.

| Heart Rate Time Series ID | Classical (Non-Fractal) Model | | | | Fractal Model | | | | |
|---|---|---|---|---|---|---|---|---|---|
| | Parameters of the model | | Goodness-of-fit | | Parameters of the model | | | Goodness-of-fit | |
| | a | b | P-value | Test statistic | α | a | b | P-value | Test statistic |
| 1 | 0.0407 | −0.0245 | 0.0018 | 0.3845 | 0.6597 | 0.5827 | 0.3508 | 0.8471 | 0.295 |
| 2 | 0.0007 | −0.0005 | 0.0031 | 0.3806 | 0.6841 | 0.7302 | 0.5853 | 0.4296 | 0.3224 |
| 3 | 0.0050 | 0.0055 | 0.0036 | 0.3795 | 0.6371 | 0.7862 | 0.8697 | 0.5523 | 0.3153 |
| 4 | 0.0289 | 0.0167 | 0.0017 | 0.3851 | 0.6307 | 0.8082 | 0.4659 | 0.226 | 0.3354 |
| 5 | −0.0225 | 0.0142 | 0.0144 | 0.3681 | 0.6516 | 0.6850 | 0.4316 | 0.5098 | 0.3178 |

TABLE II (below) is a comparison between a non-fractal model and a fractal model (see equation (4)) in terms of the estimated parameters and the goodness-of-fit obtained for five time series of heart rate activity. The R-R interval time series are obtained for individuals suffering from atrial fibrillation. All the above time series can be modeled through a fractional order differential equation as in equation (4). This is justified by the estimated p-values and test statistics.

B. Performance Analysis of Constrained Finite Horizon Fractional Optimal Control for Heart Rate Signals To illustrate the performance and efficiency of the proposed optimal controller for regulating the pacing frequency of an artificial pacemaker, we consider the heart rate of an individual suffering from atrial fibrillation (see FIG. 3a). Atrial fibrillation is a common example of irregular heart beat activity characterized by very high heart rate or very short R-R intervals. These short R-R intervals may precede congestive heart failures. To better emphasize the abnormal behavior in the length of R-R intervals, we also plot the minimum (black solid line, corresponding to 0.667 seconds) and maximum (blue dotted line, corresponding to 1 second) bounds for a normal heart rhythm. In addition, we assume that the measured heart rate comes from a CPS infrastructure where the normalized pacing frequency was set to 1 for a fixed time interval of 56 seconds corresponding to 100 recorded beats.

Both the natural and artificial pacing led to an elevated average heart rate of 108 beats per minute. The elevated heart rate is frequently experienced as heart palpitations and can cause fainting and dizziness leading to major injuries. Thus, the role of an adaptive CPS pacemaker is to regulate the pacing frequency in conjunction with the natural pacing coming from the brain in order to keep the heart rate between 60 and 90 beats per minute.

The first step in the analysis is to check which of the two modeling approaches (i.e., the non-fractal one represented by a first order differential equation and the fractal one given by a single fractional order differential equation) is more suitable to be used for capturing the heart rate characteristics exhibited for over 390 heart beats or an interval of time of 235.36 seconds. By relying on the goodness-of-fit algorithm, the P-value and test statistics for the integer first order differential equation based model are 0.0018 and 0.3845, respectively. Since we performed the null hypothesis testing at 0.05 significance value, based on small P-value of 0.0018 we can reject the integer order differential equation as being a good model. In contrast, by applying the same goodness-of-fit algorithm, the P-value and the test statistic for a fractional single order differential equation type of model are 0.8471 and 0.2949, respectively. This shows that for this interval of time, the heart rate and implicitly the R-R intervals can be better modeled via a fractional order differential equation.

Figure 3:
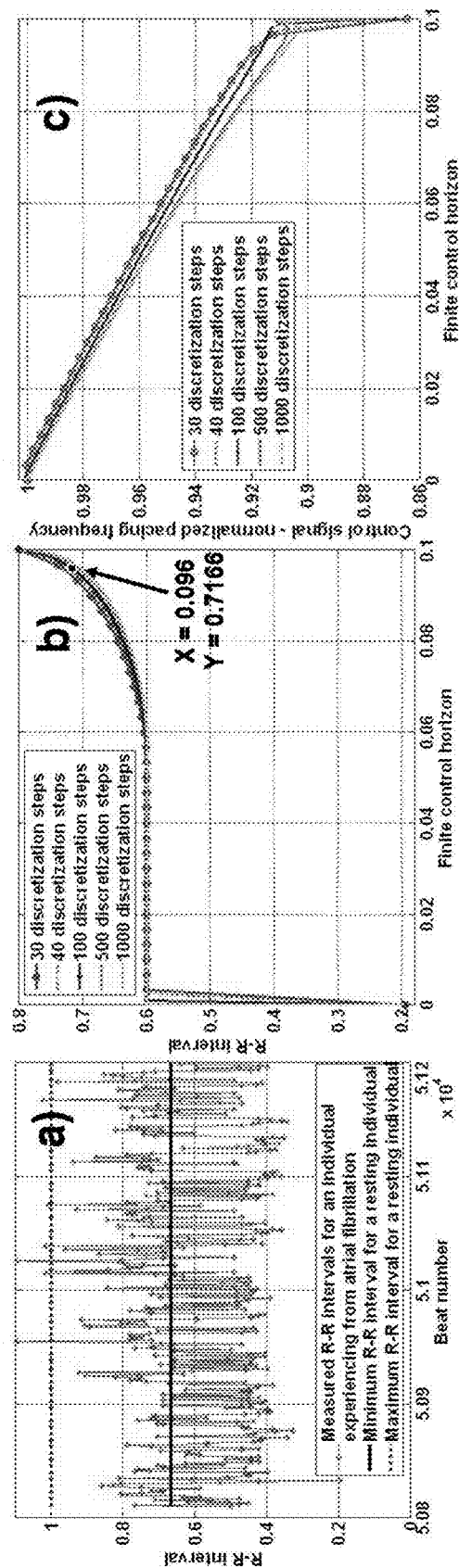
FIGS. 3a-c are plots illustrating R-R intervals. a) Illustrates a comparison between the measured R-R intervals of an individual suffering from atrial fibrillation and the minimum and maximum bounds on the R-R intervals for a healthy individual at rest. One can clearly observe that the R-R intervals have the tendency of exhibiting small magnitudes. For instance, the first 100 beats exhibit on average R-R intervals of 0.55 seconds with a standard deviation of 0.14 seconds. This can lead to palpitations and so fainting and dizziness. b) Applying the ISE fractal optimal controller given by equations (3) through (6), the R-R interval is increased from 0.19 to 0.80 (corresponding to a healthy heart rate of 75 beats per minute) in a finite control horizon of 0.1 seconds. c) Control signal—pacing frequency—necessary to be followed by the optimal control module of the pacemaker to increase the R-R intervals and reduce the heart rate from approximately 100 to 75 beats per minute.

Once the parameter identification and goodness-of-fit analysis is completed (and validate or invalidate one type of model), the role of the optimal controller in equations (3) through (6) is to determine the optimal pacing frequency for which the R-R intervals can be increased from the observed 0.20 seconds to 0.80 seconds which would correspond to a normal heart rate of 75 beats per minute. FIG. 3b shows the impact of considering various discretization steps (i.e., N=30, 40, 100, 500, and 1000 steps) on the R-R intervals for a finite control horizon of 0.1 second. Note that the controller was constrained to find the control signal such that the R-R intervals are between 0.6 and 1, and the pacing frequency between 0.5 and 1. The w and z coefficients in the performance index function shown in (3) were set to 0.1.

One can clearly see that even for a small number of discretization steps, the optimal controller is able to bring the R-R interval from 0.20 to 0.80 seconds for the predefined control horizon. In addition, FIG. 3c shows the control signal (pacing frequency) needed to be followed in parallel with the natural pacing coming from the brain to achieve a 0.8 R-R interval or a heart rate of 75 beats per minute. For completeness, the final frequency as a function of the considered number of discretization steps is as follows: 0.8745 for 1000 steps, 0.8732 for 500 steps, 0.8689 for 100 steps, 0.8658 for 40 steps and 0.8647 for 30 steps. Consequently, the loss in accuracy of computing the normalized pacing frequency from fewer discretization steps is approximately 1.1%.

Besides the importance of the number of discretization steps, the constrained finite horizon fractal optimal controller also depends on the choice of ratio between the w and z coefficients in Eq. (3). To investigate how the controller depends on this ratio, we fix the number of discretization steps and the z coefficient to 300 and 1, respectively. Next, we consider four values (i.e., 1, 5, 10, and 15) for the w coefficient and solve the optimal control problem assuming that the R-R interval state variable is constrained to be between 0.6 and 1 and the pacing frequency varies between 0.1 and 1. We also set the initial and final values for the R-R interval state variable to 0.4 and 0.8. As we can see from FIG. 4, increasing the magnitude of the w coefficient makes the state variable y(t) get closer to the reference value for the considered finite control horizon. This implies that depending on the medical conditions, the optimal controller can be customized to be more or less sensitive to deviations by adjusting the coefficients and/or the performance index in equation (3).

To fully understand the impact of the constraints on the convergence of the controller, we consider the fractal (optimal) controller defined in equations (3) through (6) for 100 discretization steps under four test cases:

a) coefficients w and z set to 1, state variable y(t) constrained between 0.79 and 1, control signal f(t) constrained between 0.01 and 1, initial value for the control signal set to 0.3, initial and final values on the state variable to 1.5 and 0.8, respectively;

b) coefficients w and z set to 1 and 0.01, respectively, state variable y(t) constrained between 0.79 and 1, control signal f(t) constrained between 0.01 and 1, initial value for the control signal set to 0.3, initial and final values on the state variable to 1.5 and 0.8, respectively;

c) coefficients w and z set to 1, state variable y(t) constrained between 0.66 and 1, control signal f(t) constrained between 0.01 and 1, initial value for the control signal set to 0.3, initial and final values on the state variable to 1.5 and 0.8, respectively;

d) coefficients w and z set to 1 and 0.01 respectively, state variable y(t) constrained between 0.79 and 1, control signal f(t) constrained between 0.01 and 1, initial value for the control signal set to 0.3, initial and final values on the state variable to 1.5 and 0.8, respectively.

Figure 5:
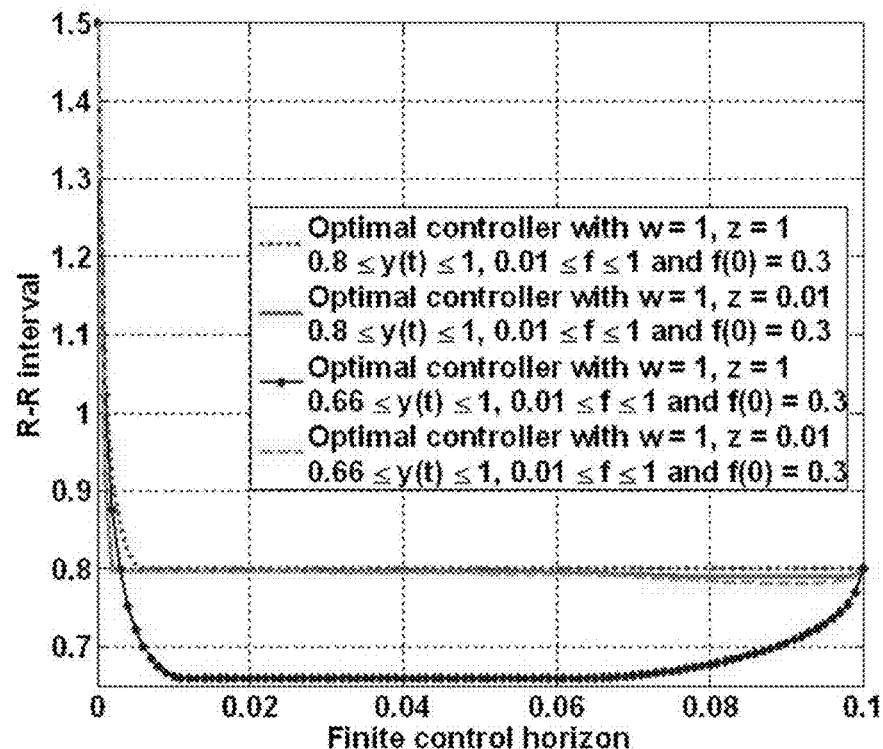
FIG. 5 is a plot illustrating the impact of the z coefficient in the performance index in (3) and the constraints imposed on the state variable y(t) while solving the constrained finite horizon fractal optimal control problem for 100 discretization steps and w=1. Decreasing the magnitude of z makes the error in the cost function more important and brings the state variable closer to the predefined reference value. Also, the constraints on state variable can influence the convergence of the controller to the reference value.

As one can observe from FIG. 5, decreasing the magnitude of z makes the error between the state variable and the reference value more significant and so contributes to a higher rate of convergence. Moreover, by comparing the green (dotted) line with the blue (star markers) curve, we can observe that the magnitude of z coefficient plays a more important role than the constraints.

Figure 6:
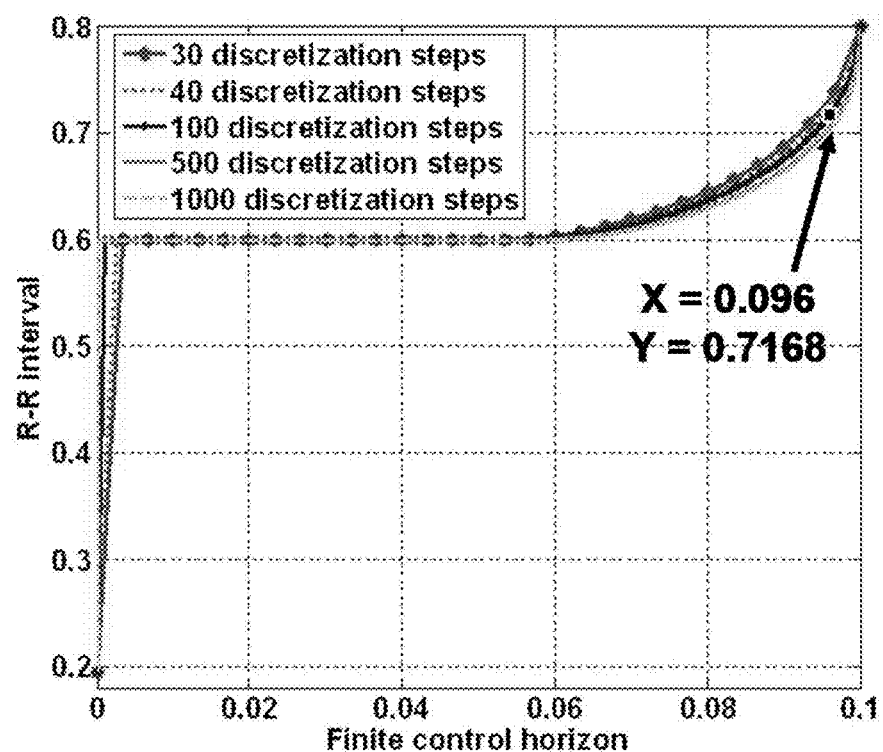
FIG. 6 is a plot illustrating the application of the ITSE fractal optimal controller described in equations (13) through (16); the R-R interval is increased from 0.19 to 0.80 (corresponding to a healthy heart rate of 75 beats per minute) in a finite control horizon of 0.1 seconds. Of note, the effect of multiplying the error between the initial and final reference value with the time it occurs forces the process to converge to the target rate a bit faster. The medical experts (Block 46) can remotely choose the ITSE fractal controller which provides a more aggressive control approach instead of the ISE fractal controller.

Next, we also considered the performance of the fractal optimal controller defined by equations (13) through (16) (where the cost function integrates the product between the time and the error between the actual and the reference R-R interval) is influenced by the number of discretization steps N. This ITSE-based constrained fractal optimal controller can be considered when prompt heart regulation is required. Note that the controller was constrained to find the control signal such that the R-R interval is kept between 0.6 and 1 seconds and the pacing frequency is between 0.5 and 1. The w and z coefficients in the performance index function shown in (3) were set to 0.1. FIG. 6 shows that the optimal controller is able to bring the R-R interval from 0.2 to 0.8 seconds in the predefined finite horizon for various discretization steps (i.e., N=30, 40, 100, 500, and 1000 discretization steps). Due to the time multiplication of the error between the actual and the reference R-R interval, this controller exhibits a slightly faster convergence to the predefined reference value.

For completeness, FIG. 6 shows the control signal (pacing frequency) needed to be followed by the optimal controller in addition to the natural pacing coming from the brain to achieve a 0.8 R-R interval or a heart rate of 75 beats per minute. In this setup, the final optimal pacing frequency is as follows: 0.8473 for 30 discretization steps, 0.8487 for 40 discretization steps, 0.8527 for 100 discretization steps, 0.8576 for 500 discretization steps, and 0.8591 for 1000 discretization steps. Consequently, by reducing the number of discretization steps from 1000 to 30 which also reduce the computational time complexity, the penalty in accuracy is less than 1.4%.

C. Theoretical Basis for a Hardware Implementation of Fractal Optimal Control

In this subsection, we describe the basis for a hardware implementation of the fractal optimal controller; we also present some illustrative results we have obtained by building an FPGA prototype.

The main idea stems from using the primal-dual interior point method for solving the linear and non-linear programming; this became popular after Karmarkar proposed a fast polynomial-time convergence of the algorithm, which makes it suitable for real time applications. This is described next:

| Primal | Dual |
|---|---|
| Minimize $c^T x$ | Maximize $b^T y$ |
| Subject to $Ax + w = b$ | Subject to $A^T y - z = c$ |
| $x, w \geq 0$ | $y, z \geq 0$ |
| Complementary conditions: | |
| $x_j z_j = 0$ | $j = 1, 2, \ldots, n$ |
| $w_i y_g = 0$ | $i = 1, 2, \ldots, m$ |

The pseudo-code for interior point method algorithm where θ is a scalar damping factor is described next:

Part 1. Start with an arbitrary guess for (x, y, w, z)
Part 2. Solve the below system of linear equations with respect to Δx, Δy, Δw and Δz:
    $A(x + \Delta x) + (w + \Delta w) = b$
    $A^T(y + \Delta y) - (z + \Delta z) = c$
    $(Z + \Delta Z)(X + \Delta X)_e = \mu_e$
    $(W + \Delta W)(Y + \Delta Y)_e = \mu_e$
Part 3. Update x, y, w, z:
    $x \Leftarrow x + \theta \Delta x$
    $y \Leftarrow y + \theta \Delta y$
    $z \Leftarrow z + \theta \Delta z$
    $w \Leftarrow w + \theta \Delta w$
Part 4. Computer $\epsilon_1$ and $\epsilon_2$:
    $\epsilon_1 = Ax + w - b$
    $\epsilon_1 = A^T y - z - c$
Part 5. If ($\epsilon_1 > \epsilon_b$ or $\epsilon_2 > \epsilon_b$)
        Go to step2.
    Else
        Finish.

The hardware implementation of the entire linear program solver consists of a data path and a finite state machine. The linear solver described in next section does part 2 of the above mentioned algorithm; part 3 and part 4 are simply vector addition and matrix-vector multiplication, respectively. Finally, a finite state machine controls the entire flow of the algorithm.

Customized Linear Solver by LU Factorization Inside Linear Solver

LU factorization algorithm for solving a system of linear equations in the form $Ax=b$ decomposes matrix A into the product of upper (U) and lower triangular (L) matrices:

$$Ax=b$$

$$LUx=b$$

The pseudo code for LU decomposition is given below:

| LU factorization algorithm |
|---|
| 1  for k = 1 to N−1 do |
| 2      for I = k + 1 to N |
| 3      do |
| 4          $a_{i,k} \leftarrow a_{i,k}/a_{k,k}$ |
| 5      end for |
| 6      for j = k + 1 to N−1 |
| 7          for I = k + 1 to N |
| 8          do |
| 9          |
| 10             $a_{i,j} \leftarrow a_{i,j} - a_{i,k} * a_{k,j}$ |
|         end for |
|     end for |
| end for |

Figure 4:
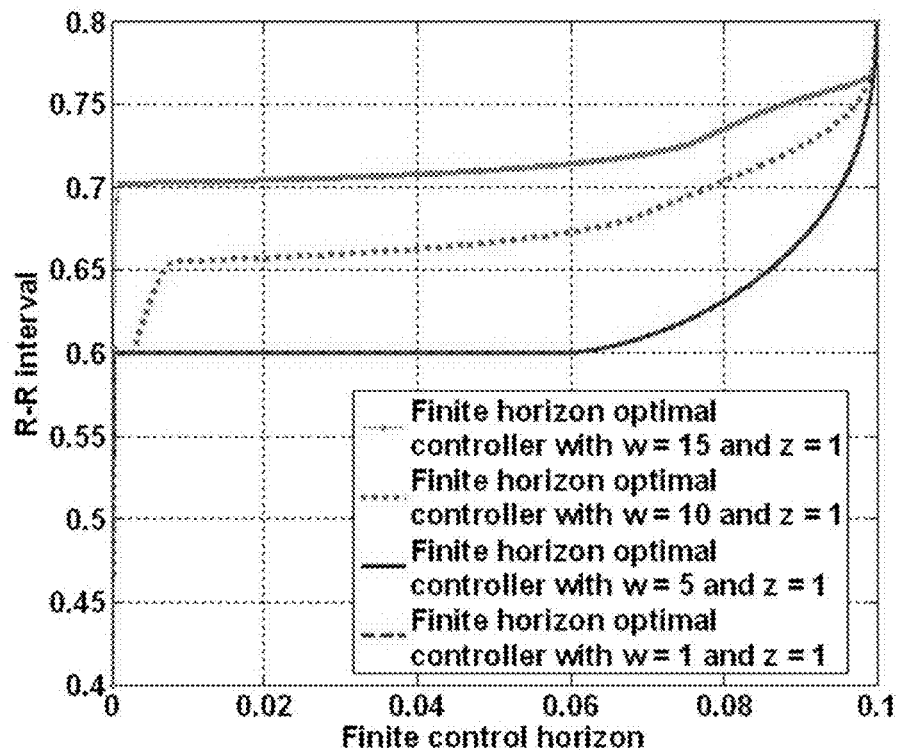
FIG. 4 is a plot illustrating the impact of the w coefficient in the performance index in (3) on solving the constrained finite horizon fractal optimal control problem for 300 discretization steps and z=1. Increasing the magnitude of w makes the error in the cost function larger and brings the state variable closer to the predefined reference value.

FIG. 4. LU Factorization Algorithm

This algorithm replaces the U and L matrices in place of the original matrix. Matrix U is stored in the lower diagonal elements of A without explicitly mentioning that upper diagonal elements of this matrix are zero and diagonal elements of U are all one. The same is applied to L, but its non-zero elements are stored in upper triangular elements of A.

The unknown variables of the system of equations inside primal-dual interior point are Δx, Δy, Δw and Δz. An appropriate ordering of these variables makes the coefficient matrix A in linear system of equations in a format that makes the complexity of the factorization algorithm less than what it is in general. Also, it eliminates the use of divide operations in line 3 of FIG. 4, which not only speeds up the algorithm, but also makes this algorithm appropriate for hardware realization since dividers are expensive in hardware. Below, we show the best ordering of the unknown variables and the coefficient matrix corresponding to the ordering.

| 1 0<br>0 1 | | A | |
|---|---|---|---|
| 1 0<br>0 1 | −1 0 0<br>0 −1 0<br>0 0 −1 | | $A^\tau$ |
| | $X_2$ 0 0<br>0 … 0<br>0 0 $X_N$ | $Z_2$ 0 0<br>0 … 0<br>0 0 $Z_N$ | |
| $Y_2$ 0<br>0 $Y_m$ | | | $W_2$ 0<br>0 $W_m$ |

Line 3 of the algorithm, requires division of all elements below diagonal by the corresponding diagonal element in each clumn. However, as can be seen from above, there is no need for divide operation here and only negation of $X_i$ elements is enough and the rest of lower diagonal elements remain unchanged.

The for loop in line 5 of FIG. 4 can be broken into first n, n+m and m+2n iterations. The above matrix A is a depiction after these iterations and shows the modified matrix A after m+2n steps of the factorization algorithm. The first m+n iterations are easy to understand. If either of the $A_{kj}$ or $A_{ik}$ elements at each iteration of the line 7 of the algorithm are zero, then the $A_{ij}$ of the elements in the submatric in line 7 loop of the algorithm remains unchanged. This is why elements in the n+1 till 2n row leave unchanged.

General Solver for Linear System of Equations

A system of linear equations is often presented as $Ax=b$ where A is an N×N coefficient matrix and unknown variables are represented in N-element vector (x). There are two main classes of linear solvers: iterative and direct. Iterative methods do not guarantee convergence and hence are not good choice for real time applications.

Among direct solvers, including factorization methods and Cramer method, we have chosen Cramer method with Chio's condensation for determinant calculation and show how hardware realization of Chio's condensation method combined with the mirroring technique makes it the most superior among implementation of all directed method solvers from performance point of view.

Cramer's rule states that each component of the solution to the linear equation of the form $Ax=b$ (where A is invertible) is given by:

$$x_i = det(A_i(b))/det(A)$$

Where $(A_i(b))$ denotes the matrix A with its ith column replaced by b. Chio's condensation for determinant calculation reduces a matrix of order N to order N−1 and so on. Chio's pivotal condensation theorem says:

$$|A| = |D|/a_{11}^{n-2}$$

Given that $a_{11} \neq 0$ and $|D|$ denote the matrix $A=[a_{ij}]$ obtained by replacing each $a_{ij}$ element not in the lead row or column by $$\begin{vmatrix} \alpha_{11} & \alpha_{1j} \\ \alpha_{i1} & \alpha_{ij} \end{vmatrix}.$$

Considering that we only need the ratio of the original matrix determinant and the modified matrix, at each condensation step, we factor out the powers of a values in each condensation step.

At each step k of the condensation, all remaining matrix elements $a_{ij}$ except the elements in lead row and lead column are replaced by $$\begin{vmatrix} \alpha_{kk} & \alpha_{kj} \\ \alpha_{ik} & \alpha_{ij} \end{vmatrix}.$$

This does not depend on the order of the computation among different elements and hence can be done in parallel.

The hardware architecture proposed consists of address selection logic and computation logic. Corresponding to each element, there are two multipliers and an adder which perform the 2×2 determinant calculation and address generating logic determines the operands of the calculation which are $a_{kk}$, $a_{kj}$ and $a_{ik}$. There are also N dividers needed for computation on the last condensation step.

Computation of the determinant by parallel architecture finishes after N−1 step condensation while sequential software computation requires $O(N^3)$ steps, since:

$$\Sigma_{k=1}^{N-1} 2(N-k)^2 + (N-k) = 2N^3/3 - N^2/2 - N/6 \in O(N^3) \tag{$N^3$}$$

Simple application of Cramer's rule requires repeating the computation of $det(A_i(b))$ for every unknown or having multiple hardware architectures running in parallel for every unknown. The first one results in total run time of $O(N^2)$ and $O(N^2)$ hardware complexity associated with each element of the matrix while the second approach results in $O(N^2)$ run time as well as $O(N^3)$ hardware complexity and hence power consumption.

However, by the mirroring technique, substitution of column vector b is delayed in order to use common computations for multiple variables. In this technique, b must be subject to the same condensation computations that would occur had it already been replaced. As the condensation removes the information associated with discarded columns, the variables associated with those columns cannot be computed once condensed. For this reason, a mirror of the matrix is created in the first step as well as each time the matrix is halved. The mirror is identical to the original matrix except the order of its column is reversed.

Below, we show how the computation on the second column of the matrix is identical in the first condensation step for both matrixes where b is substituted in the fourth and third column.

The mirroring technique can be done in hardware by mirroring the remaining matrix to the space of the discarded columns.

Below, we show how mirroring is done when the condensation step reaches N/2 step and how this technique preserves the initial N×2N space and does not need extra memory and hardware architecture. In this manner, after N−1 iteration of the condensation steps, the linear program algorithm computes all N unknown variables with a dividing operation in the last step which is computed as follows $x_i = b_{i,i}/a_{Ni}$. This figure depicts the entire condensation process till the calculation of all unknown variables for a simple 4×4 system of equation.

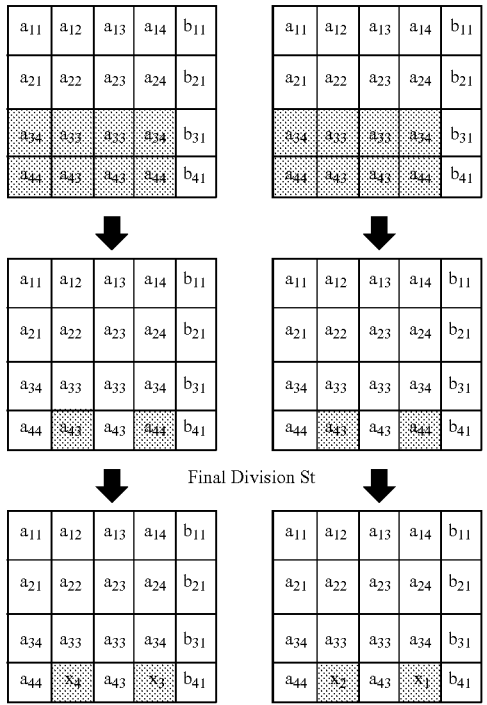

Final Division St

The proposed hardware architecture for solving a linear system of equations is superior to previous implementations of direct methods from performance point of view, as well as numerical stability:

Assuming no significant clock cycle difference between this and factorization based algorithms, this method computes all unknown variables after N cycle while the factorization methods use backward and forward substitutions which make the final value of unknown variables after 3N clock cycles.

a) Unlike factorization-based algorithms, the use of divide operation is delayed until the last step of the algorithm. This prevents error propagation through the algorithm steps, as the divide operation is more expensive.
b) Factoring out the powers of the a values prevents numerical instability and overflow.

Synthesis Results

We synthesized on Xilinx Virtex 7 FPGA for problem size of 32×32 and here we report the results:

Timing constraint: Default period analysis for Clock 'Clk' Clock period: 2.162 ns (frequency: 462.610 MHz)

| Slice Logic Utilization | Used | Available | Utilization |
|---|---|---|---|
| Number of Slice Registers | 32 | 408,000 | 1% |
| Number used as Flip Flops | 32 | | |
| Number used as Latches | 0 | | |
| Number used as Latch-thrus | 0 | | |
| Number used as AND/OR logics | 0 | | |
| Number of Slice LUTs | 71 | 204,000 | 1% |
| Number used as logic | 70 | 204,000 | 1% |
| Number using O6 output only | 39 | | |
| Number using O5 output only | 30 | | |
| Number using O5 and O6 | 1 | | |
| Number used as ROM | 0 | | |
| Number used as Memory | 0 | 70,200 | 0% |
| Number used exclusively as route-thrus | 1 | | |
| Number with same-slice register load | 0 | | |
| Number with same-slice carry load | 1 | | |
| Number with other load | 0 | | |
| Number of occupied Slices | 21 | 51,000 | 1% |
| Number of LUT Flip Flop pairs used | 71 | | |
| Number with an unused Flip Flop | 39 | 71 | 54% |
| Number with an unused LUT | 0 | 71 | 0% |
| Number of fully used LUT-FF pairs | 32 | 71 | 45% |
| Number of unique control sets | 2 | | |
| Number of slice register sites lost to control set restrictions | 8 | 408,000 | 1% |
| Number of bonded IOBs | 258 | 600 | 43% |
| Number of RAMB36E1/FIFO36E1s | 0 | 750 | 0% |
| Number of RAMB18E1/FIFO18E1s | 0 | 1,500 | 0% |
| Number of BUFG/BUFGCTRLs | 1 | 32 | 3% |
| Number used as BUFGs | 1 | | |

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

We claim:

1. A method for non-linear (fractional dynamics) modeling of physiological behavior measured by an implantable device, comprising the steps of:
    measuring the physiological behavior;
    determining magnitude of deviation between the measured physiological behavior and a reference value $y^{ref}$;
    modeling dynamics of the measured physiological behavior with continuous time fractional differential equations to identify parameters of a non-linear fractal model;
    selecting a constrained fractal optimal control problem;
    deriving optimality conditions for the constrained fractal optimal control problem when the magnitude of deviation exceeds a predetermined threshold;
    discretizing the optimality conditions for the constrained fractal optimal control problem; and
    solving the constrained fractal optimal control problem corresponding to the optimality conditions to identify an optimal physiological behavior to operate the implantable device.

2. The method according to claim 1, wherein in the physiological behavior is an R-R interval.

3. The method according to claim 1, wherein the implantable device is a pacemaker.

4. The method according to claim 1, wherein the step of deriving optimality conditions for the constrained fractal optimal control problem comprises using wavelets and linear regression.

5. The method according to claim 1, wherein the step of selecting a constrained fractal optimal control problem comprises the step of selecting a finite time fractal optimal control with integral of squared tracking error criterion.

6. The method according to claim 1, wherein the step of selecting a constrained fractal optimal control problem comprises the step of selecting a finite time fractal optimal control with integral of squared time multiplied by squared tracking error criterion.

7. The method according to claim 1, wherein the step of determining magnitude of deviation between the measured physiological behavior and a reference value comprises analyzing the magnitude of a state variable y(t) minus the reference valve $y^{ref}$.

8. The method according to claim 1, wherein the state variable y(t) is an R-R interval.

9. The method according to claim 1, wherein the step of deriving optimality conditions for the constrained fractal optimal control problem when the magnitude of deviation exceeds a predetermined threshold, comprises the step of solving the following equations:

$$\min_{f(t)} \int_{t_i}^{t_f} \left\{ \frac{w}{2}[y(t) - y^{ref}(t)]^2 + \frac{z}{2}f^2(t) \right\} dt$$

$$\frac{d^\alpha y(t)}{dt^\alpha} = a(t)y(t) + b(t)f(t),$$

$$y(t_i) = y_0, \; y(t_f) = y_0, \; 0 \leq y^{min} \leq y(t) \leq y^{max} \leq 1$$

$$f^{min} \leq f(t) f^{max}$$

where y(t) represents the heart rate activity seen as a state variable, $y^{ref}(t)$ denotes the reference value, f(t) is the pacing frequency, w and z are the weighting coefficients for the quadratic error and magnitude of the control signal, respectively, in the cost function, $\alpha$ is the exponent of the fractional order derivative characterizing the dynamics of the heart rate activity y(t), a(t) and b(t) are weighting coefficients for the heart activity and pacing frequency, $y^{min}$ and $y^{max}$ are the minimum and maximum bounds on heart rate activity y(t), $y(t_i)$ is the initial condition, $y(t_f)$ is the final condition, $f^{min}$ and $f^{max}$ are the minimum and maximum allowed bounds on pacing frequency f(t);

$$L = \int_{t_i}^{t_f} \left\{ \frac{w[y(t) - y^{ref}(t)]^2}{2} + \frac{zf^2(t)}{2} + \beta_1(f - f^{min} - \xi_1) -- \right.$$

$$\left. \lambda\left[\frac{d^\alpha y(t)}{dt^\alpha} - a(t)y(t) - b(t)f(t)\right] + \beta_2(f^{max} - f - \xi_2) \right\} dt$$

where $\lambda$, $\beta_1$, and $\beta_2$ are the Lagrange multipliers associated with the dynamical state equation for y(t) and the constraints imposed on the control variable f, $\xi_1$ and $\xi_2$ are the slack variables needed to transform the inequality bounds into equality constraints on the control variable f; and $$\frac{\partial L}{\partial y} + {}_tD^\alpha_{t_f}\frac{\partial L}{\partial_{t_i}D^\alpha_t y} = 0, \; \frac{\partial L}{\partial f} = 0, \; \frac{\partial L}{\partial \lambda} = 0, \; \frac{\partial L}{\partial \beta_1} = 0, \; \frac{\partial L}{\partial \beta_2} = 0$$

where ${}_{t_i}D^\alpha_t$ and ${}_tD^\alpha_{t_f}$ are the fractional derivatives operating backward and forward in time, respectively.

10. The method according to claim 1, wherein the step of solving the constrained fractal optimal control problem corresponding to the optimality conditions to identify an optimal physiological behavior to operate the implantable device, comprises the step of solving the following equations:

$$y(t_i) = y_0, \; y(t_f) = y_0, \; 0 \leq y^{min} \leq y(t) \leq y^{max} \leq 1$$

$$f^{min} \leq f(t) \leq f^{max}$$

where y(t) represents the heart rate activity seen as a state variable, f(t) is the pacing frequency, $y^{min}$ and $y^{max}$ are the minimum and maximum bounds on heart rate activity y(t), $y(t_i)$ is the initial condition, $y(t_f)$ is the final condition, $f^{min}$ and $f^{max}$ are the minimum and maximum allowed bounds on pacing frequency f(t); and $$\sum_{i=0}^{k} \frac{(-1)^i}{\Delta t^\alpha}\binom{\alpha}{i} y((k-i)\Delta t) - a(k\Delta t)y(k\Delta t) + \frac{b(k\Delta t)}{z(k\Delta t)}\lambda(k\Delta t) +$$

$$\frac{b(k\Delta t)}{z(k\Delta t)}\beta_1(k\Delta t) - \frac{b(k\Delta t)}{z(k\Delta t)}\beta_2(k\Delta t) = 0, \; k = 1, \ldots, N$$

$$\frac{\beta_2(k\Delta t) - \beta_1(k\Delta t) - b(k\Delta t)\lambda(k\Delta t)}{z(k\Delta t)} - \xi_1(k\Delta t) = f^{min}, \; k = 1, \ldots, N$$

$$\frac{\beta_2(k\Delta t) - \beta_1(k\Delta t) - b(k\Delta t)\lambda(k\Delta t)}{z(k\Delta t)} + \xi_2(k\Delta t) = f^{max}, \; k = 1, \ldots, N$$

$$\sum_{i=0}^{N-k}\binom{\alpha}{i}\frac{(-1)^i\lambda((k+i)\Delta t)}{\Delta t^\alpha} - w(k\Delta t)[y(k\Delta t) - y^{ref}(k\Delta t)] -$$

$$a(k\Delta t)\lambda(k\Delta t) + \frac{\lambda(\Delta tN)(t_f - t_i - k\Delta t)^{-\alpha}}{\Gamma(1-\alpha)} = 0, \; k = N-1, \ldots, 0$$

which computes the y and $\lambda$ values for a predefined set of discretization steps.

11. The method according to claim 1, wherein the step of deriving optimality conditions for the constrained fractal optimal control problem when the magnitude of deviation exceeds a predetermined threshold, comprises the step of solving the following equations:

$$\min_{f(t)} \int_{t_i}^{t_f} \left\{ \frac{w}{2}[t(y(t) - y^{ref}(t))]^2 + \frac{z}{2}f^2(t) \right\} dt$$

$$\frac{d^\alpha y(t)}{dt^\alpha} = a(t)y(t) + b(t)f(t),$$

$$y(t_i) = y_0, \; y(t_f) = y_0, \; 0 \leq y^{min} \leq y(t) \leq y^{max} \leq 1$$

$$f^{min} \leq f(t) f^{max}$$

where y(t) represents the heart rate activity seen as a state variable, $y^{ref}(t)$ denotes the reference values that need to be achieved in terms of heart rate activity, f(t) is the pacing frequency, w and z are the weighting coefficients for the quadratic error and magnitude of the control signal, respectively, in the cost function, $\alpha$ is the exponent of the fractional order derivative characterizing the dynamics of the heart rate activity y(t), a(t) and b(t) are weighting coefficients for the heart activity and pacing frequency, $y^{min}$ and $y^{max}$ are the minimum and maximum bounds on heart rate activity y(t), $y(t_i)$ is the initial condition, $y(t_f)$ is the final condition, $f^{min}$ and $f^{max}$ are the minimum and maximum allowed bounds on pacing frequency f(t);

$$L = \int_{t_i}^{t_f} \left\{ \frac{w[y(t) - y^{ref}(t)]^2}{2} + \frac{zf^2(t)}{2} + \beta_1(f - f^{min} - \xi_1) - \lambda\left[\frac{d^\alpha y(t)}{dt^\alpha} - a(t)y(t) - b(t)f(t)\right] + \beta_2(f^{max} - f - \xi_2) \right\} dt$$

where $\lambda$, $\beta_1$, and $\beta_2$ are the Lagrange multipliers associated with the dynamical state equation for $y(t)$ and the constraints imposed on the control variable f, $\xi_1$ and $\xi_2$ are the slack variables needed to transform the inequality bounds into equality constraints on the control variable f; and $$\frac{\partial L}{\partial y} + {}_t D_{t_f}^\alpha \frac{\partial L}{\partial_{t_i} D_t^\alpha y} = 0, \frac{\partial L}{\partial f} = 0, \frac{\partial L}{\partial \lambda} = 0, \frac{\partial L}{\partial \beta_1} = 0, \frac{\partial L}{\partial \beta_2} = 0$$

where ${}_t D_t^\alpha$ and ${}_t D_{t_f}^\alpha$ are the fractional derivatives operating backward and forward in time, respectively.

12. The method according to claim 1, wherein the step of solving the constrained fractal optimal control problem corresponding to the optimality conditions to identify an optimal physiological behavior to operate the implantable device, comprises the step of solving the following equations:

$$y(t_i) = y_0, y(t_f) = y_0, 0 \leq y^{min} \leq y(t) \leq y^{max} \leq 1$$

$$f^{min} \leq f(t) \leq f^{max}$$

where $y(t)$ represents the heart rate activity seen as a state variable, $y^{ref}(t)$ denotes the reference values that need to be achieved in terms of heart rate activity, $f(t)$ is the pacing frequency, w and z are the weighting coefficients for the quadratic error and magnitude of the control signal, respectively, in the cost function, $\alpha$ is the exponent of the fractional order derivative characterizing the dynamics of the heart rate activity $y(t)$, $a(t)$ and $b(t)$ are weighting coefficients for the heart activity and pacing frequency, $y^{min}$ and $y^{max}$ are the minimum and maximum bounds on heart rate activity $y(t)$, $y(t_i)$ is the initial condition, $y(t_f)$ is the final condition, $f^{min}$ and $f^{max}$ are the minimum and maximum allowed bounds on pacing frequency $f(t)$; and $$\sum_{i=0}^{k} \frac{(-1)^i}{\Delta t^\alpha} \binom{\alpha}{i} y((k-i)\Delta t) - a(k\Delta t)y(k\Delta t) + \frac{b(k\Delta t)^2}{z(k\Delta t)} \lambda(k\Delta t) + \frac{b(k\Delta t)\beta_1(k\Delta t)}{z(k\Delta t)} - \frac{b(k\Delta t)\beta_2(k\Delta t)}{z(k\Delta t)} = 0, k = 1, \ldots, N$$

$$\sum_{i=0}^{N-k} \binom{\alpha}{i} \frac{(-1)^i \lambda((k+i)\Delta t)}{\Delta t^\alpha} - w(k\Delta t)(k\Delta t)^2 [y(k\Delta t) - y^{ref}(k\Delta t)] - a(k\Delta t)\lambda(k\Delta t) + \frac{\lambda(\Delta t N)(t_f - t_i - k\Delta t)^{-\alpha}}{\Gamma(1-\alpha)} = 0, k = N-1, \ldots, 0$$

$$\frac{\beta_2(k\Delta t) - \beta_1(k\Delta t) - b(k\Delta t)\lambda(k\Delta t)}{z(k\Delta t)} - \xi_1(k\Delta t) = f^{min}, k = 1, \ldots, N$$

$$\frac{\beta_2(k\Delta t) - \beta_1(k\Delta t) - b(k\Delta t)\lambda(k\Delta t)}{z(k\Delta t)} + \xi_2(k\Delta t) = f^{max}, k = 1, \ldots, N$$

which computes the y and $\lambda$ values for a predefined set of discretization steps.

* * * * *